US006376723B2

(12) United States Patent
Drent et al.

(10) Patent No.: US 6,376,723 B2
(45) Date of Patent: Apr. 23, 2002

(54) PROCESS FOR THE CARBONYLATION OF FORMALDEHYDE

(75) Inventors: Eit Drent; Wilhelmus Petrus Mul; Bart Johan Ruisch, all of Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/739,172

(22) Filed: Dec. 18, 2000

(30) Foreign Application Priority Data

Dec. 29, 1999 (EP) .............................................. 99310623

(51) Int. Cl.$^7$ ........................ C07C 27/00; C07C 69/00; C07C 69/66
(52) U.S. Cl. ..................... 568/864; 568/861; 560/129; 560/179
(58) Field of Search ................................ 568/864, 861; 560/179, 129

(56) References Cited

U.S. PATENT DOCUMENTS

| | | | |
|---|---|---|---|
| 2,152,852 A | 4/1939 | Loder | 260/535 |
| 2,285,448 A | 6/1942 | Loder | 260/635 |
| 3,795,712 A | 3/1974 | Torck et al. | 260/671 C |
| 3,911,003 A | 10/1975 | Suzuki | 260/535 R |
| 4,024,203 A | 5/1977 | Torck et al. | 260/683.15 A |
| 4,087,470 A | 5/1978 | Suzuki | 568/864 |
| 4,933,410 A | 6/1990 | Okrongly | 525/333.6 |

FOREIGN PATENT DOCUMENTS

DE 31 07 518 A1 10/1981

OTHER PUBLICATIONS

International Search Report of Jun. 6, 2001.
"Carbonlylation of Formaldehyde Over Ion Exchange Resin Catalysts. 1. Batch Reactor Studies," by Lee, Kim, Lee and Kim, *Ind. Eng. Chem. Res.* 1993, vol. 32, pp. 253–259.
"The Proton: Applications to Organic Chemistry," by Ross Stewart, (1985), published by Academic Press, Inc. ISBN 0–12–670370–1.
Ullmann's Encyclopedia of Industrial Chemistry, vol. A9, 1987, pp. 572–575.

*Primary Examiner*—Sreeni Padmanabhan
*Assistant Examiner*—Elvis O. Price

(57) ABSTRACT

A carbonylation process, wherein formaldehyde or a derivative thereof is reacted with carbon monoxide in the presence of a catalyst composition including:

a) an acidic compound with pKa value below –1, and
b) a sulfone.

15 Claims, No Drawings

PROCESS FOR THE CARBONYLATION OF FORMALDEHYDE

This invention relates to a carbonylation process, wherein formaldehyde or a derivative thereof is reacted with carbon monoxide in the presence of a catalyst system.

BACKGROUND OF THE INVENTION

The carbonylation of formaldehyde yields as its main and most desirable product (poly)glycolic acid, which acid can for example be easily esterified with an alcohol and then catalytically hydrogenated to produce ethylene glycol. Ethylene glycol (EG) is one of the most important of the commercially available glycols. It is predominantly used in antifreeze and in the production of polyesters. Presently, EG is commercially produced by the liquid phase hydration of ethylene oxide (EO), which in turn is produced by oxidation of ethene. The economy of the conventional process is highly dependent on the ethylene price. The dependence on ethylene as raw material has promoted the investigation of alternative EG production processes based on synthesis gas (syngas), which is a less expensive feedstock.

DuPont is the only company that actually operated a syngas based EG synthesis route in a commercial plant from 1940 to 1968. The commercial DuPont process used formaldehyde derived from syngas as raw material and sulphuric acid as the catalyst. In this process, formaldehyde was first carbonylated with carbon monoxide and water to hydroxyacetic acid (glycolic acid) at 200° C. and 700 bar. The glycolic acid was subsequently esterified with methanol to form methyl glycolate and water. The methyl glycolate was hydrogenated to EG with accompanying release of methanol. The DuPont process gave a 90% molar yield based on formaldehyde during the carbonylation step. Relevant DuPont patent publications are U.S. Pat. No. 2,152,852 (1939) and U.S. Pat. No. 2,285,448 (1942).

In U.S. Pat. No. 3,911,003 to Chevron (1975) there is disclosed a similar process for preparing glycolic acid by the reaction of formaldehyde with carbon monoxide (as such or in syngas) and water in the presence of HF at about 22–50° C. and 1000–2000 psig (about 6800–13800 pKa). Glycolic acid is obtained in 95% selectivity and at about 100% formaldehyde conversion. It is mentioned that the glycolic acid can be esterified with methanol and then catalytically hydrogenated to produce a mixture of ethylene glycol and diethylene glycol which is readily separated by distillation.

U.S. Pat. No. 4,087,470 to Chevron (1978) presents an alternative to the glycolic acid esterification step for producing ethylene glycol from formaldehyde, by using ethylene glycol instead of methanol. It defines an integrated process for preparing ethylene glycol by (1) contacting formaldehyde and syngas in the presence of HF to deplete the carbon monoxide from the syngas and simultaneously form glycolic and diglycolic acid, (2) contacting the acid product with ethylene glycol, diethylene glycol or a mixture thereof to produce the respective glycolates, (3) removing residual carbon monoxide from the carbon monoxide depleted syngas of step 1 to produce a hydrogen-rich gas, (4) hydrogenating the glycolates with the hydrogen-rich gas to produce the respective glycols, and (5) recycling a portion of the glycols to step 2.

The Chevron process for carbonylating formaldehyde represents an improvement over the DuPont process in that the required temperature is lower, but the pressure is still very high.

In the article of Lee, Kim, Lee and Kim, Carbonylation of formaldehyde over Ion Exchange Resin Catalysts. 1. Batch Reactor Studies, Ind. Eng. Chem. Res., 1993, vol. 32, pages 253–259, a similar process for acid-catalysed carbonylation of formaldehyde to glycolic acid and its esterification to obtain methylglycolate is disclosed. As acid-catalyst, several sulfonic acid resins, including NAFION NR-50, AMBERLYST 15 and AMBERLYST 36 were mentioned. As solvents 1,4-dioxane, acetic acid, methyl benzoate, methyl formate, methyl acetate, formic acid, methanol and methylene chloride were mentioned. It was found that except for acid solvents, all solvents showed better selectivity towards methylglycolate in the presence of water. Maximum methylglycolate yields of about 78% were obtained at a temperature of about 135° C. However, to obtain such a yield, a high initial CO pressure of 3500 psig (about 24100 kPa) was needed.

In U.S. Pat. No. 4,933,410 to Applied Immunosciences (1990) there is disclosed a method for functionalising polystyrene surfaces of labware by contacting polystyrene surfaces with an a-substituted N-hydroxymethyl acetamide compound, dissolved in tetramethylene sulfone (sulfolane), in the presence of a Lewis acid (including protonic catalysts), such as trifluoromethane sulfonic acid.

In U.S. Pat. No. 3,795,712 (1974) and U.S. Pat. No. 4,024,203 (1977), both to Institut Francais du Petrole, there are disclosed a hydrocarbon alkylation process and a monoolefin oligomerisation process respectively, both in the presence of a liquid catalyst composition containing a Lewis acid or a Brønsted acid and a sulfone (such as sulfolane).

SUMMARY OF THE INVENTION

The present invention relates to a carbonylation process, wherein formaldehyde or a derivative thereof is reacted with carbon monoxide in the presence of a catalyst composition including:
  a) an acidic compound with pKa value below −1,
  b) a sulfone.

DETAILED DESCRIPTION OF THE INVENTION

It has now been found that by using a catalyst composition of an acid and a sulfone, the carbonylation of formaldehyde or a derivative thereof can be conducted under relatively mild reaction conditions.

The process according to the present invention can be used for the carbonylation of formaldehyde or a derivative thereof. A preferred group of derivatives of formaldehyde includes dimethoxy methane, dioxolane, trioxane (trioxymethylene) and the polymer para-formaldehyde. Formaldehyde and para-formaldehyde are particularly preferred. The carbonylation product, (poly)glycolic acid, can be used for producing ethylene glycol via the known steps of esterification and hydrogenation.

Another preferred group of derivatives of formaldehyde are the acetals and poly-acetals. Suitable acetals include the hemi-acetals. The dimethyl acetal of formaldehyde is preferred. The carbonylation product of the dimethyl acetal of formaldehyde, methoxy methyl acetate, can be an interesting chemical solvent, gasoline octane booster or diesel supplement. Polyacetal is a suitable acetal alternative to formaldehyde in the production of ethylene glycol as above.

The acidic compound to be used in the catalyst composition in the carbonylation process according to the invention has a pKa below −1, preferably below −2, when measured in water at a temperature of 18° C. Said acidic compound may be homogeneous or heterogeneous and can be any kind of Lewis acid or Brønsted acid.

The term "pKa" is a common symbol used to express the strength of an acid and is related to the dissociation constant for the acid in aqueous solution. The measurement and evaluation of pKa for a wide range of strong and weak acid types is reviewed in "The Proton: Applications to Organic Chemistry" by Ross Stewart, (1985), published by Academic Press, Inc. ISBN 0-12-670370-1.

Preferred homogeneous acids may suitably be chosen from the group of sulfonic acids. Preferably the homogeneous acid is an halogenated sulfonic acid of the R—$SO_3H$ type, wherein R represents an halogenated aliphatic or an halogenated aromatic group. An especially preferred halogenated sulfonic acid is triflic acid (trifluoromethylsulfonic acid).

The homogeneous acid can also be a combination of acids, such as a superacid. Suitable superacid systems include $HFBF_4$ and $HSbF_6$.

Preferred heterogeneous acids are the strongly acidic ion exchange resins, all of which are of the sulphonic type. Examples of commercially available strongly acidic ion exchange resins of the sulphonic type are those known by the trade names AMBERLYST 15, AMBERLYST 38 W, AMBERLYST 36, AMBERJET 1500H, AMBERJET 1200H, (AMBERJET is a trademark of Rohm and Haas Company) DOWEX MSC-1, DOWEX 50W (DOWEX is a trademark of Dow Chemical Company), DELOXAN ASP I/9 (DELOXAN is a trademark of Degussa), DIANON SK1B (DIANON is a trademark of Mitsubishi), LEWATIT VP OC 1812, LEWATIT S 100 MB, LEWATIT S 100 G1 (LEWATIT is a trademark of Bayer), NAFION SAC13, NAFION NR50 (NAFION is a trademark of DuPont) and CT275 (a macroporous resin with a medium pore diameter in the range of from 600 to 750, available from Purlite).

When a heterogeneous acid is used in the process of the invention, this has the advantage of easier separation from the reaction product.

The sulfone to be used in the catalyst composition in the carbonylation process according to the invention is preferably of the formula $R^1$—$SO_2$—$R^2$, wherein $R^1$ and $R^2$ independently represent a monovalent hydrocarbon group such as an aliphatic, cyclo-aliphatic or aromatic group, containing from 1 to 12 carbon atoms or wherein $R^1$ and $R^2$ together form a bivalent hydrocarbon group containing from 3 to 12 carbon atoms. Examples of sulfones are those wherein $R^1$ and $R^2$ are alkyl and/or aryl groups, such as dimethylsulfone, di-n-propylsulfone, ethylmethylsulfone and diphenylsulfone. Preferred sulfones are the alicyclic sulfones wherein the $SO_2$ group is inside a hydrocarbon ring, $R^1$ and $R^2$ together forming a branched or unbranched bivalent hydrocarbon group. Suitable alicyclic sulfones include sulfolane (tetramethylene sulfone), 3-methyl sulfolane, and 2,4-dimethyl sulfolane.

Other components may also be present in the catalyst system utilised in the present invention, for example inert or reactive solvents. As an example of reactive solvents, carboxylic acids, in particular acetic acid, may be mentioned. It is thought that the combination of acetic acid and sulfolane as solvent, utilised with an acidic compound of pKa value below −1 in a carbonylation process of the present invention, would be especially favorable and may well yield increased carbonylation selectivity.

In the carbonylation process according to the present invention, a certain amount of water may be present. Although water tends to decrease the conversion rate, it may increase the selectivity towards a specific product, such as for example poly-glycolic acid. The optimum amount of water depends on factors known to one skilled in the art, such as the temperature, the pressure and the type and amount of catalyst and formaldehyde source used. The concentration of water should be less than 30% (w/w) based on the total weight of sulfone and water, preferably less than 20% (w/w) more preferably in the range between 0% and 10%, especially from 0.1 to 5, and more especially from 0.5 to 2 (w/w).

The amount of acidic compound to be used in the process of the present invention can vary between wide ranges. Suitably the molar ratio of acidic compound to equivalents of monomer formaldehyde is in the range of 1:1000 to 100:1 (i.e. 0.001 to 100), preferably in the range of 1:100 to 10:1 (i.e. 0.01 to 10), for both the homogeneous and the heterogeneous type of acid. Mol equivalents of monomer formaldehyde is defined as mol formaldehyde derivative times the number of units of formaldehyde from which the formaldehyde compound is built up. For example trioxane consists of 3 units of formaldehyde and thus one mol of trioxane equals 3 mol of equivalents monomer formaldehyde.

The amount of sulfone to be used in the process of the present invention can vary within wide ranges. Suitably the molar ratio of sulfone to equivalents of monomer formaldehyde is between 1:1 to 100:1, preferably between 1:1 and 50:1.

When the acidic compound is of the homogeneous type, it is suitably dissolved in the sulfone. The concentration of acidic compound in the sulfone can vary between wide ranges but is preferably within a range from 0.001 M to 10 M, more preferably within a range from 0.01 M to 1.0 M, and most preferably within a range from 0.05 M to 0.5 M.

Residence time in the reaction vessel can vary dependent on factors such as the specific type acidic compound and sulfone used and their respective concentration, the formaldehyde feed and the temperature and pressure applied. Optimally the residence time is as short as possible, even in the range of minutes. When the carbonylation is performed as a batch-wise process, suitably the residence times are up to 15 hours, preferably in the range of from 1 minute to 10 hours, more preferably in the range of from 10 minutes to 8 hours. When the carbonylation is performed as a continuous flow process, the Liquid Hourly Space Velocity will suitably be in the range of 0.050 to 20 l, preferably in the range of 0.050 to 7 l, of feed per liter of effective reactor volume per hour (l/l.h).

Reaction pressures may be atmospheric or superatmospheric. In particular the pressures are conveniently in the range of from 100 to 10000 kPa. Carbon monoxide partial pressures can vary in the range of from 100 to 10000 kPa, preferably from 2000 to 9000 kPa. The carbon monoxide can be used in its pure form or mixed with hydrogen, preferably as syngas, or it may be formed in situ out of the formaldehyde during the reaction. The carbon monoxide can be diluted with an inert gas such as nitrogen, carbon dioxide or one or more of the noble gases such as argon.

The carbonylation reaction is conveniently carried out at a moderate temperature, generally ranging from 20 to 170° C., preferably ranging from 40 to 140° C.

When formaldehyde, its trimer or polymer, are carbonylated according to the present invention to produce (poly) glycolic acid, this product can be further processed to ethylene glycol by esterification and hydrogenation according to known methods.

The esterification step may be performed by generally known processes, such as described in for example Ullmann's encyclopedia of Industrial Chemistry Volume, A9, 1987, pages 572–575. As described in U.S. Pat. No. 4,087,470 the esterification step can be performed with a monohydric alcohol such as methanol or with a polyhydric alcohol such as ethylene glycol and/or diethylene glycol. The esterification step is typically acid-catalysed; and either the same acidic catalyst composition to that utilised for the carbonylation reaction, or a conventional esterification catalyst, may be used to catalyse such a subsequent esterification. Suitable esterification reaction conditions are a temperature in the range of 10 to 250° C. and pressure in the range of 10 to 1500 kPa. Suitably the esterification is carried out at reflux.

The hydrogenation step may be performed by generally known processes. As also described in U.S. Pat. No. 4,087,470 the hydrogenation step is performed in the presence of a catalyst which is preferably a metal oxide. Suitable ester hydrogenation reaction conditions comprise a temperature in the range of 125–325° C. and pressure in the range of 1000 to 20000 kPa.

The process of the present invention therefore also relates to a process for producing ethylene glycol comprising:

a) carbonylating formaldehyde or a derivative thereof as described hereinabove to produce glycolic acid or polyglycolic acid;

b) esterification of the (poly)glycolic acid with methanol to produce methyl glycolate; and c) hydrogenation of the methyl glycolate to produce ethylene glycol.

The following examples will illustrate certain specific aspects of the invention but are not intended to limit its broader scope.

EXAMPLES

General Procedure

1. Carbonylation

Examples 1–6, 9–16 and A were conducted in a 250 ml stirred stainless-steel autoclave. Examples 7, 8 and 17–26 and B were conducted in a similar 500 ml autoclave. The autoclave was charged with substrate, acidic compound and solvent (i.e. sulfolane, or diglyme (diethyl glycol dimethyl ether), or water) and subsequently closed and evacuated. After evacuation the autoclave was pressurised with carbon monoxide and heated. After a pre-determined residence time the carbonylation reaction was terminated by releasing the pressure.

Conversion in the carbonylation reaction was determined by carbon monoxide consumption in Examples 1–6, 9–16 and A and by substrate consumption in Examples 7, 8 and 17–26 and B.

2. Trans-esterification

In Examples 1–6, 9–16 and A the contents of the autoclave after carbonylation were poured in 50 ml of methanol and refluxed during 5 hours, to transesterify the (poly) glycolic acid into methyl glycolate. In experiments 7, 8 and 17–26 the contents of the autoclave after carbonylation were poured into 150 ml of methanol and refluxed during 5 hours, to transesterify the (poly)glycolic acid into methyl glycolate.

In experiment B 10 ml of the contents of the autoclave after carbonylation were poured in 100 ml of methanol and refluxed during 5 hours.

The selectivity towards methyl glycolate HO—$CH_2$—C(O)—$OCH_3$ was determined by gas-liquid chromatography. The main by-product found was its dimer $CH_3O$—C(O)—$CH_2$—O—$CH_2$—C(O)—$OCH_3$.

The Examples 1–16 and Comparative Examples A–B and their results are summarised in the following Table 1 and Table 2.

Examples 17–20 and 21–26, relating to the influence of the acidic compound to formaldehyde ratio and the water content and their results, are summarised in Table 3 and 4 respectively.

TABLE 1

Examples 1–14 illustrate the use of both heterogeneous and homogeneous catalysts and the use of several formaldehyde sources. Example 2 illustrates that a mixture of CO and $H_2$, such as syngas, can be used as a source of carbon monoxide. Comparative examples A and B illustrate that the use of a sulfone, such as sulfolane, as a solvent is essential.

| Example | Substrate | Solvent (ml) | Acidic compound (pKa, mmol) | T (° C.) | P CO (*$10^2$ kPa) | t (hr) | Conversion after carbonylation (%) | Selectivity towards methylglycolate after esterification (%) |
|---|---|---|---|---|---|---|---|---|
| 1 | Para formaldehyde (7.5 g) | sulfolane (50) | triflic acid (−5.7, 10) | 100 | 30 | 0.4 | 100 | 75 |
| 2 | Para formaldehyde (7.5 g) | sulfolane (50) | triflic acid (−5.7, 10) | 100 | 25 + 30 $H_2$ | 0.4 | 100 | 75 |
| 3 | Para formaldehyde (7.5 g) | sulfolane (50) | triflic acid (−5.7, 10) | 70 | 30 | 1 | 100 | 85 |
| 4 | Polyacetal (7.5 g) | sulfolane (50) | triflic acid (−5.7, 10) | 100 | 30 | 0.3 | 100 | 75 |
| 5 | Para formaldehyde (7.5 g) | sulfolane (50) | triflic acid (−5.7, 2) | 100 | 30 | 3 | 95 | 72 |
| 6 | Para formaldehyde (7.5 g) | sulfolane (50) | NAFION (NR50) (≦−2.7, 8) | 100 | 60 | 3 | 85 | 90 |
| 7 | Para formaldehyde (15 g) | sulfolane (150) | NAFTON (SAC13) (≦−2.7, 1) | 80–120 | 40–50 | 5 | 25 | 91 |
| 8 | Para formaldehyde (15 g) | sulfolane (150) | AMBERLYST 38 W (≦−2.7, 193) | 100 | 50 | 4.2 | 100 | 78 |

TABLE 1-continued

Examples 1–14 illustrate the use of both heterogeneous and homogeneous catalysts and the use of several formaldehyde sources. Example 2 illustrates that a mixture of CO and $H_2$, such as syngas, can be used as a source of carbon monoxide. Comparative examples A and B illustrate that the use of a sulfone, such as sulfolane, as a solvent is essential.

| Example | Substrate | Solvent (ml) | Acidic compound (pKa, mmol) | T (° C.) | P CO ($*10^2$ kPa) | t (hr) | Conversion after carbonyl-ation (%) | Selectivity towards methyl-glycolate after esterification (%) |
|---|---|---|---|---|---|---|---|---|
| 9 | Para formaldehyde (7.5 g) + 0.5 g $H_2O$ | sulfolane (50) | triflic acid (−5.7, 10) | 100 | 60 | 4 | 100 | 88 |
| 10 | Polyacetal chips (7.5 g) + 0.5 g $H_2O$ | sulfolane (50) | NAFION (NR50) (≦−2.7, 8) | 100 | 60 | 5 | 95 | 93 |
| 11 | Para formaldehyde (7.5 g) | sulfolane (50) | perfluoro benzene-sulfonic acid (<−2.7, 5) | 100 | 60 | 6 | 60 | 94 |
| 12 | trioxane (7.5 g) | sulfolane (50) | perfluoro benzene-sulfonic acid (<−2.7, 5) | 100 | 60 | 5 | 90 | 90 |
| 13 | Para formaldehyde (7.5 g) | sulfolane (50) | $HSbF_6$ (<−5, 11) | 70 | 50 | 0.2 | 100 | 74 |
| 14 | Para formaldehyde (7.5 g) | sulfolane (50) | methylsulfonic acid (−1.9, 100) | 100 | 40 | 5 | 40 | not determined |
| A | Para formaldehyde (7.5 g) | diglyme (50) | triflic acid (−5.7, 10) | 110 | 30 | 5 | None | — |
| B | Para formaldehyde (15 g) | water (150) | sulphuric acid (−1.98, 90) | 100 | 50 | 4 | None | — |

TABLE 2

Examples 15 and 16 illustrate carbonylation of derivatives of formaldehyde leading to other carbonylation products than glycolic acid or polyglycolic acid. Example 16 illustrates the carbonylation of dioxolane to 2-oxo-1,4-dioxane. The later is a precursor in the preparation of biodegradable polymers

| Example | substrate | Solvent (ml) | Acidic compound (pKa, mmol) | T (° C.) | P CO ($*10^2$ kPa) | t (hr) | Conversion after carbonylation (%) |
|---|---|---|---|---|---|---|---|
| 15 | dimethoxy methane (10 ml) | sulfolane (50) | triflic acid (−5.7, 10) | 70 | 50 | 0.2 | 95% to 1,2-dimethoxy 1-oxo ethane ($CH_3OCH_2C(O)OCH_3$) |
| 16 | dioxolane (10 ml) | sulfolane (50) | triflic acid (−5.7, 10) | 40 | 80 | 5 | 10% to 2-oxo 1,4 dioxane |

TABLE 3

Examples 17–20 illustrate that high conversions can be obtained at different molar ratios acidic compound to substrate. The examples were all conducted at a temperature of 100° C. and a CO pressure of 5000 kPa during 250 minutes.

| Example | substrate | Solvent (ml) | Acidic compound (mmol) | Molar ratio of acidic compound to substrate | Conversion after carbonylation (%) | Selectivity towards methyl-glycolate after esterification |
|---|---|---|---|---|---|---|
| 17 | Para formaldehyde (250 mmol) | sulfolane (150) | AMBERLYST 38 W (99 mmol) | 0.87 | 98 | 84 |

TABLE 3-continued

Examples 17–20 illustrate that high conversions can be obtained at different molar ratios acidic compound to substrate. The examples were all conducted at a temperature of 100° C. and a CO pressure of 5000 kPa during 250 minutes.

| Example | substrate | Solvent (ml) | Acidic compound (mmol) | Molar ratio of acidic compound to substrate | Conversion after carbonylation (%) | Selectivity towards methyl-glycolate after esterification |
|---|---|---|---|---|---|---|
| 18 | Para formaldehyde (500 mmol) | sulfolane (150) | AMBERLYST 38 W (108 mmol) | 0.44 | 87 | 95 |
| 19 | Para formaldehyde (500 mmol) | sulfolane (150) | AMBERLYST 38 W (193 mmol) | 0.87 | 100 | 78 |
| 20 | Para formaldehyde (1000 mmol) | sulfolane (150) | AMBERLYST 38 W (193 mmol) | 0.44 | 97 | 81 |

TABLE 4

Examples 21–26 show that a certain amount of water may be present in the carbonylation process and that its presence may increase selectivity. The examples were all conducted at a temperature of 100° C. and a CO pressure of 5000 kPa during 250 minutes.

| Example | substrate | Solvent (g) | Acidic compound (mmol) | water (mmol, g) | water percentage (% w/w) in solvent | Conversion after carbonylation (%) | Selectivity towards methyl-glycolate after esterification |
|---|---|---|---|---|---|---|---|
| 21 | Para formaldehyde (250 mmol) | sulfolane (189) | AMBERLYST 38 W (99) | 0, 0 | 0 | 97 | 90 |
| 22 | Para formaldehyde (250 mmol) | sulfolane (189) | AMBERLYST 38 W (98) | 56, 1 | 0.5 | 98 | 95 |
| 23 | Para formaldehyde (250 mmol) | sulfolane (189) | AMBERLYST 38 W (98) | 111, 2 | 1.0 | 88 | 96 |
| 24 | Para formaldehyde (250 mmol) | sulfolane (189) | AMBERLYST 38 W (99) | 167, 3 | 1.6 | 79 | 98 |
| 25 | Para formaldehyde (250 mmol) | sulfolane (189) | AMBERLYST 38 W (197) | 167, 3 | 1.6 | 97 | 96 |
| 26 | Para formaldehyde (220 mmol) | sulfolane (189) | AMBERLYST 38 W (190) | 2610, 47 | 19.9 | 58 | 69 |

Example 27

This example illustrates the use of in-situ produced CO as a source for CO.

A 500 ml magnetically stirred stainless-steel autoclave was charged with 150 ml sulfolane, 15 g para-formaldehyde and 35.3 g (192 mmol) dried AMBERLYST 38W. The autoclave was closed, without adding gasses, and heated to 160° C. while its contents were stirred. After 250 minutes the contents of the autoclave were poured into 150 ml methanol and refluxed during 5 hours, to transesterify the (poly) glycolic acid into methyl glycolate.

98% of the para-formaldehyde was converted (conversion was determined by substrate consumption).

The selectivity towards methyl glycolate was determined by gas-liquid chromatography. The main products found were 55% methyl glycolate, 2.6% dimer of methylglycolate and 41% methyl methoxy acetate.

We claim:

1. A carbonylation process wherein formaldehyde or a derivative thereof is reacted with carbon monoxide in the presence of a catalyst composition comprising:
   a) an acidic compound with pKa value below −1; and
   b) a sulfone.

2. The process of claim 1 wherein the derivative of formaldehyde is paraformaldehyde.

3. The process of claim 1 wherein the sulfone is according to the formula $$R^1-SO_2-R^2,$$

wherein $R^1$ and $R^2$ independently represent a monovalent hydrocarbon group such as an aliphatic, cyclo-aliphatic or aromatic group containing from 1 to 12 carbon atoms, or wherein $R^1$ and $R^2$ together form a bivalent hydrocarbon group containing from 3 to 12 carbon atoms.

4. The process of claim 1 wherein the acidic compound is an homogeneous acid.

5. The process of claim 4 wherein the acidic compound is of the R—SO$_3$H type, wherein R represents a halogenated alkyl or an halogenated aromatic group.

6. The process of claim 1 wherein the acidic compound is an heterogeneous acid.

7. The process of claim 6 wherein the heterogeneous acid is a strongly acidic ion exchange resin.

8. The process of claim 1 wherein also water is present in a concentration of less than 30% (w/w) based on the total weight of sulfone and water.

9. The process of claim 1 wherein the molar ratio of acidic compound to equivalents of monomer formaldehyde or a derivative thereof is in the range of 1:100 to 10:1.

10. A process for producing ethylene glycol comprising:
   a) carbonylating formaldehyde or a derivative thereof with carbon monoxide according to the process of claim 1 to produce glycolic acid or polyglycolic acid;
   b) esterification of the (poly) glycolic acid with methanol to produce methyl glycolate; and
   c) hydrogenation of the methyl glycolate to produce ethylene glycol.

11. The process of claim 10 wherein the derivative of formaldehyde is paraformaldehyde.

12. The process of claim 10 wherein the sulfone is according to the formula $$R^1\text{—}SO_2\text{—}R^2,$$

wherein $R^1$ and $R^2$ independently represent a monovalent hydrocarbon group such as an aliphatic, cyclo-aliphatic or aromatic group containing from 1 to 12 carbon atoms, or wherein $R^1$ and $R^2$ together form a bivalent hydrocarbon group containing from 3 to 12 carbon atoms.

13. The process of claim 12 wherein the acidic compound is an homogeneous acid.

14. The process of claim 12 wherein the acidic compound is an heterogeneous acid.

15. The process of claim 10 wherein the molar ratio of acidic compound to equivalent of monomer formaldehyde or a derivative thereof is in the range of 1:100 to 10:1.

* * * * *